US007828787B2

(12) United States Patent
Brandenburger et al.

(10) Patent No.: US 7,828,787 B2
(45) Date of Patent: Nov. 9, 2010

(54) CONNECTOR FOR PACKAGING CONTAINING MEDICAL FLUIDS AND PACKAGING FOR MEDICAL FLUIDS

(75) Inventors: Torsten Brandenburger, Niddatal (DE); Ismael Rahimy, Friedberg (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 967 days.

(21) Appl. No.: 10/514,817

(22) PCT Filed: Feb. 24, 2003

(86) PCT No.: PCT/EP03/01847

§ 371 (c)(1), (2), (4) Date: Apr. 20, 2005

(87) PCT Pub. No.: WO03/099191

PCT Pub. Date: Dec. 4, 2003

(65) Prior Publication Data

US 2005/0215943 A1 Sep. 29, 2005

(30) Foreign Application Priority Data

May 27, 2002 (DE) ................................ 102 23 560

(51) Int. Cl.
*A61M 5/32* (2006.01)

(52) U.S. Cl. ........................ 604/411; 604/408; 604/409; 604/410; 383/107; 383/109; 206/219; 206/486

(58) Field of Classification Search .......... 604/408–411
See application file for complete search history.

(56) References Cited

U.S. PATENT DOCUMENTS 3,136,440 A 6/1964 Krug et al. .................... 215/47
3,900,028 A 8/1975 McPhee ...................... 128/272
4,516,977 A * 5/1985 Herbert ...................... 604/415
5,088,995 A 2/1992 Packard et al. .............. 604/415
5,259,843 A * 11/1993 Watanabe et al. ........... 604/256

(Continued)

FOREIGN PATENT DOCUMENTS

DE 14 98 600 3/1941

(Continued)

OTHER PUBLICATIONS

English machine translation of DE 100 30 474 C1.*

(Continued)

*Primary Examiner*—Tatyana Zalukaeva
*Assistant Examiner*—Ilya Y Treyger
(74) *Attorney, Agent, or Firm*—Kenyon & Kenyon LLP

(57) ABSTRACT

The disclosure relates to a connector for packaging containing medical fluids, in particular infusion or transfusion bags, including a tubular connection part for receiving a spike for the withdrawal of fluid, and having a lower opening on the packaging side and an upper opening on the connection side. A self-sealing membrane, which is pierced by the spike, is located in the connection part. The membrane has an upper, annular section leading into a lower, plate-shaped section, said annular section of the membrane surrounding the spike in a sealing manner, when the latter pierces the plate-shaped section. The membrane acts as a guide for the spike and also reseals the connector, once the spike has been removed.

19 Claims, 3 Drawing Sheets

U.S. PATENT DOCUMENTS

| | | | | |
|---|---|---|---|---|
| 5,896,989 | A * | 4/1999 | Ropiak et al. | 206/438 |
| 6,039,718 | A * | 3/2000 | Niedospial, Jr. | 604/408 |
| 6,893,428 | B2 * | 5/2005 | Willemstyn | 604/533 |

FOREIGN PATENT DOCUMENTS

| | | | |
|---|---|---|---|
| DE | 35 43 825 | A1 | 6/1986 |
| DE | 197 28 775 | A1 | 1/1999 |
| DE | 694 16 696 | T2 | 9/1999 |
| DE | 100 30 474 | C1 * | 2/2002 |
| EP | 737 058 | B1 | 10/1996 |
| WO | WO 95/17873 | | 7/1995 |
| WO | WO 96/23545 | | 8/1996 |

OTHER PUBLICATIONS

International Preliminary Examination Report in PCT/EP03/01847 dated Mar. 23, 2004.

* cited by examiner

CONNECTOR FOR PACKAGING CONTAINING MEDICAL FLUIDS AND PACKAGING FOR MEDICAL FLUIDS

This is the U.S. national phase of International Application No. PCT/EP03/01847 filed Feb. 24, 2003, the entire disclosure of which is incorporated herein by reference.

BACKGROUND OF THE DISCLOSURE

1. Field of the Disclosure

The disclosure relates to a connector for packaging containing medical fluids, in particular infusion or transfusion bags, which serves to inject or extract a fluid from the bag. Moreover, the disclosure relates to packaging for medical fluids, in particular an infusion or transfusion bag, with such a connector.

2. Related Technology

WO 96/23545 describes an infusion bag with an injection part and an extraction part. The injection part serves to feed a drug by means of an injection syringe. It comprises a tubular connection part, which is sealed by a protective cap designed as a break-off part. A self-sealing septum sits in the opening area of the connection part, whilst a membrane capable of being pierced is arranged in the connection part, so that the septum does not come into contact with the solution before the use of the infusion bag. The extraction part serves to extract the solution by means of a spike. The extraction part does not have a self-sealing septum, but otherwise the structure is similar to that of the injection part.

A connector for the extraction of an infusion solution is also described in DE 197 28 775 C2. The tubular connection part of the known extraction part is sealed by a flat membrane, which is in one piece with the connection part.

SUMMARY OF THE DISCLOSURE

The known extraction parts have been tried and tested in practice. A drawback, however, consists in the fact that the infusion bag is not sealed again after the spike has been withdrawn. There is therefore the risk of the infusion solution running out. This is particularly critical after the addition of cytostatic drugs.

A further drawback is that the connection between the spike and the extraction part is not secured against slipping out. When the bag is hanging on the stand, there is the risk of the connection of the spike and the extraction part being separated due to unintentional tugging on the flexible-tube line.

There is also the drawback that the injected membrane, which seals the connection part of the extraction part, does not always withstand greater mechanical loads. Thus, it has been shown in drop tests that the membrane of individual extraction parts ruptured.

The problem underlying the disclosure is to provide a connector for packages containing medical fluid, in particular infusion or transfusion bags, which reliably seals the packaging after the withdrawal of the spike.

Accordingly, the disclosure provides a connector for packages containing medical fluids, including a tubular connection part for receiving a spike for the extraction of the fluid, the connection part having upper and lower openings, a break-off sealing part, a self-sealing membrane that can be pierced by the spike for the extraction of the fluid and having a circular upper portion, which transforms into a dish-shaped lower portion to form a trough-shaped recess, wherein a portion of the membrane sealingly surrounds the spike when the spike pierces the dish-shaped portion.

DETAILED DESCRIPTION

Figure 1:
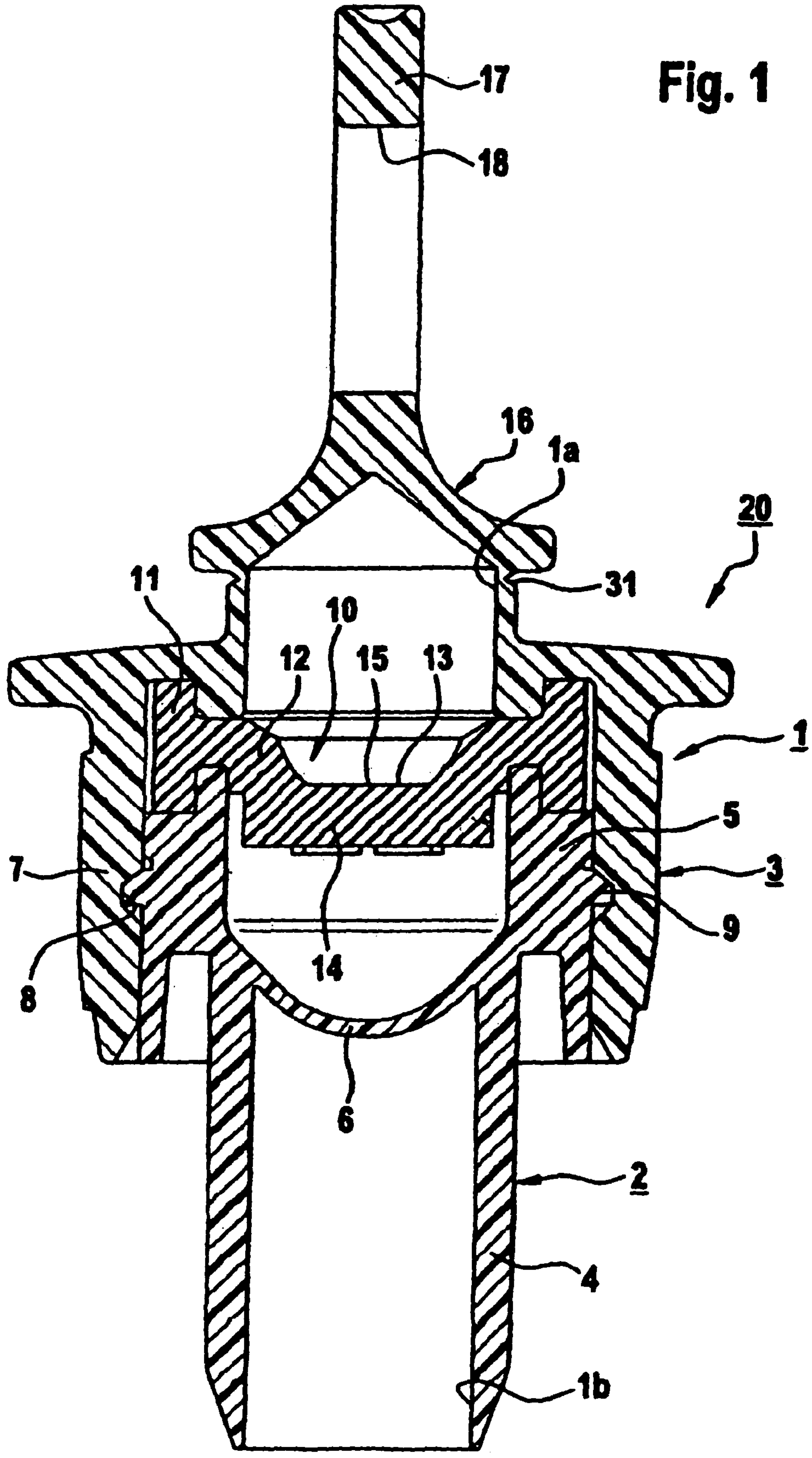
FIG. 1 illustrates a connector designed as an extraction part for packages containing medical fluids in sectional representation.

The connector according to the disclosure has a self-sealing membrane, which is arranged in the connection part for accommodating the spike for the extraction of the fluid. The self-sealing membrane prevents the fluid from running out of the packaging after withdrawal of the spike.

It is advantageous that the self-sealing membrane has a circular portion, which is continuous with a dish-shaped portion, whereby the circular portion of the membrane surrounds the spike in a sealed manner when it pierces the dish-shaped portion.

The special formation of the membrane with the circular and dish-shaped portion ensures that the spike is guided reliably when it pierces the membrane and guarantees that the membrane is again reliably sealed after withdrawal of the spike even in the presence of relatively high internal pressure in the packaging. It has been shown in tests that the special formation of the membrane is decisive for immediate resealing, whereby the sealing of the membrane is further enhanced with increasing pressure in the packaging. The reliable sealing can be traced back not to the volume of material, but to the special geometry of the membrane.

In a preferred embodiment of the connector according to the invention, the material of the dish-shaped portion of the membrane is weakened, so that the membrane can be particularly easily pierced by the spike. The membrane is preferably pre-slit in the form of a cross. It can also be pre-slit in the form of a star or the like or only be provided with a simple slit.

In a particularly preferred embodiment, the tubular connection part of the connector consists of a lower and an upper section, whereby the sections are fixed in a snap-in manner. The self-sealing membrane is preferably held clamped with elastic deformation between the lower and upper section. Consequently, the fitting of the connector can be carried out in a straightforward manner by pressing together the individual parts. It is however also possible for the individual parts to be welded and/or glued together.

A further particularly preferred embodiment makes provision such that an outer portion, which is clamped between the upper and lower sections, is continuous with the circular portion of the membrane.

In order to prevent the self-sealing membrane in the tubular connection part from coming into contact with the solution contained in the infusion or transfusion bag prior to use, a second membrane capable of being pierced is preferably arranged beneath the self-sealing membrane thereby forming an intermediate space. The second membrane is expediently a one-piece component of the tubular connection part.

It has been shown in tests that the use of a membrane curved upwards or downwards instead of a flat membrane leads to an increase in drop strength. Since the second membrane is designed curved upwards or downwards, the connector according to the invention withstands relatively great mechanical loads. Apart from the increase in drop strength, there is also the advantage that the spike in the pierced position is held clamped by the curved membrane. The retention force of the spike in the withdrawal position is thus increased, as a result of which unintentional slipping out is prevented.

In order to secure the upper and lower part of the connection piece against radial torsion, both parts can have toothing or the like, which also ensures precise alignment of the parts during pressing together. Furthermore, the risk of damage to the two membranes is especially low during the pressing together of the individual parts.

The break-off sealing part of the connector, which serves as an originality seal, is preferably connected to the connection part via a circular rupture zone.

Since the break-off sealing part preferably has a grip part, which is designed in the manner of an arrow pointing upwards, it can immediately be recognized that the connector is an extraction part, but not an injection part. Preferably, the arrow is a recess in the grip part, which is immediately recognizable without lettering or the like being necessary. Confusion between the extraction and injection part of a package containing medical fluids can thus be avoided.

The lower part of the connection part also preferably has an arrow pointing upwards, which is designed as a raised structure, preferably in a recessed grip. The upward-pointing arrow of the lower part also permits the connector to be unequivocally assigned as the extraction part after breaking-off the sealing part.

An example of an embodiment is explained in greater detail below by reference to the drawings.

Connector 20 designed as an extraction part for packages containing medical fluids, in particular infusion or transfusion bags, has a tubular connection part 1, which includes a package-side lower section 2 and a connection-side upper section 3. Tubular connection part 1 therefore has an upper and a lower opening 1*a*, 1*b*. Connector 20 is an injection-molded part made of polypropylene.

Lower section 2 of tubular connection part 1 has a lower cylindrical portion 4, which is continuous with an upper sleeve-shaped portion 5. Cylindrical portion 4 of lower section 2 can be inserted into a connection socket of a film bag and can be welded or glued to the socket or be directly welded into the film bag without a socket. Cylindrical portion 4 is sealed at its upper end with a membrane 6 capable of being pierced, said membrane being a single-piece component of lower section 2. The injected membrane 6 is curved downwards. Alternatively, however, the membrane 6 can also be curved upwards.

Upper section 3 of tubular connection part 1 is fixed in a snap-in manner on lower section 2, whereby upper section 3 has a cylindrical portion 7 which surrounds lower section 2. The internal wall of cylindrical portion 7 of upper section 3 has a peripheral groove 8, into which a peripheral projection 9 on the outer wall of sleeve-shaped portion 5 of lower section 2 snaps when the two sections 2, 3 are pressed together.

A self-sealing membrane 10 made of an elastic material, which is also referred to as a septum, is held clamped with elastic deformation between the lower and upper section 2, 3 of tubular connection part 1. Self-sealing membrane 10 has an outer portion 11, which is clamped between lower and upper sections 2, 3 of circular connection part 1. Outer portion 11 is followed by an upper circular portion 12, which is continuous with a lower dish-shaped portion 14 thereby forming a trough-shaped recess 13 at the upper side of membrane 10. Dish-shaped portion 14 is pre-slit in the form of a cross or a star in center 15, so that the elastic material is weakened, but is not severed.

Upper section 3 of tubular connection part 1 is followed, via a circular rupture zone 31, by a cap-shaped sealing part 16, which seals upper opening 1*a* of connection part 1. Sealing part 16 is continuous with a flat grip part 17, which is provided with a recess 18 in the shape of an arrow 19 pointing upwards. It can immediately be recognized from the direction of arrow 19 that connector 20 is not injection part 40, but rather the extraction part.

Figure 2:
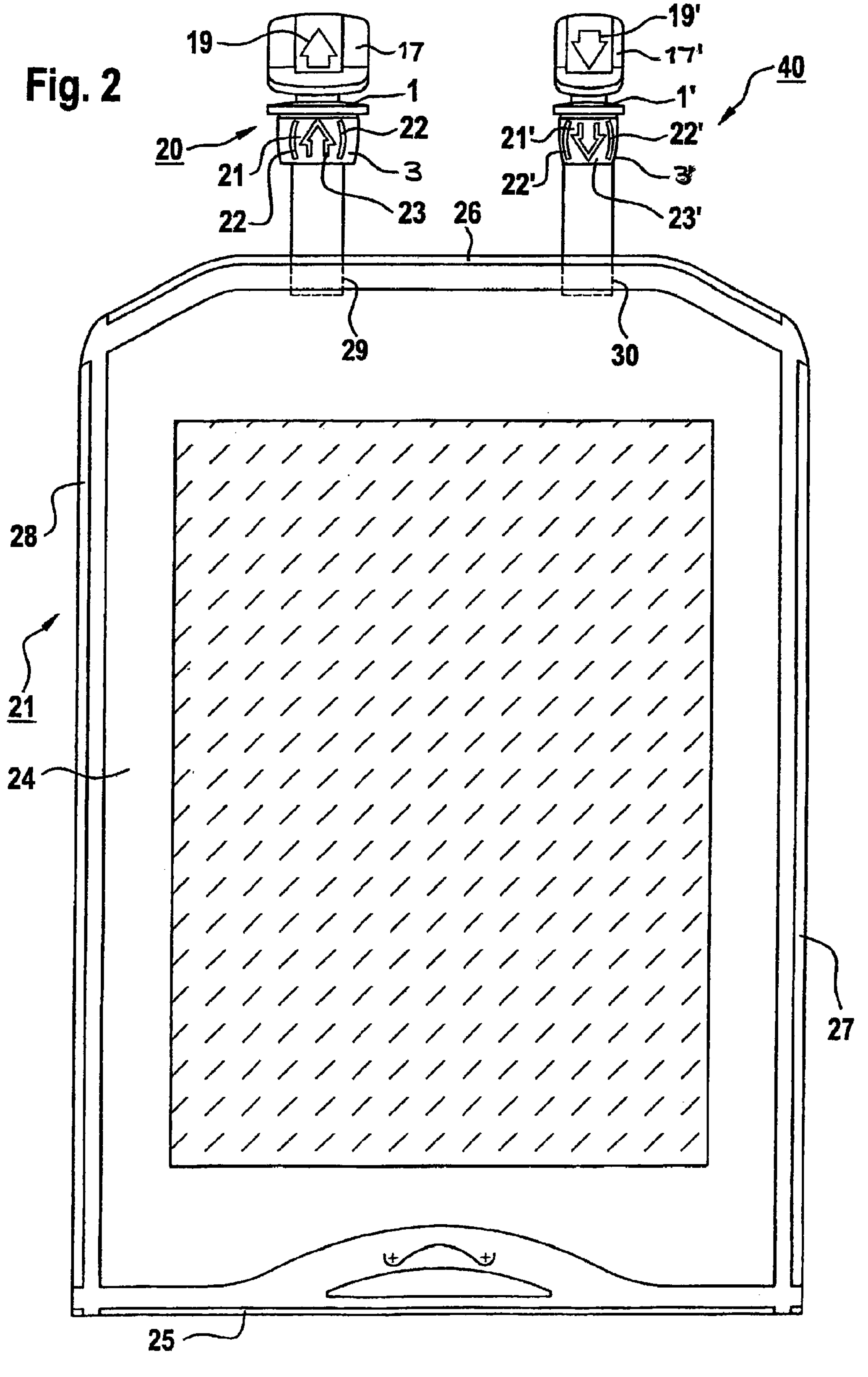
FIG. 2 illustrates an infusion bag with the extraction part of FIG. 1 and an injection part and FIG. 3 illustrates the injection part of the infusion bag of FIG. 2 in sectional representation.

The side view of connector 20 of FIG. 1 is shown in FIG. 2. FIG. 2 shows an infusion bag 21 filled with infusion solution, which has connector 20 for the extraction of the infusion solution and a further connector 40 for the injection of a solution into infusion bag 21.

On the outer wall of cylindrical portion 7 of upper section 3, tubular connection part 1 of connector 20 has two recessed grips 21 lying opposite one another, which are each formed by projecting webs 22 which are arranged at a distance from one another. A further arrow 23, which also points upwards in order to identify connector 20 as the extraction part, is formed as a raised structure on the outer wall of cylindrical portion 7 between webs 22.

Infusion bag 21 comprises two film layers 24, which are welded together at lower and upper edge 25, 26 and also at longitudinal edges 27, 28. Two connections sockets 29, 30 are welded into upper edge 26 of the infusion bag. The tubular connection pieces of injection and extraction part 40, 20 are inserted into connection sockets 30, 29, respectively and connected with the sockets during sterilization. The tubular connection pieces of the originality seals can however also be molded onto an insert that is round or designed in the manner of a boat, said insert being welded in between the two film layers 24.

Figure 3:
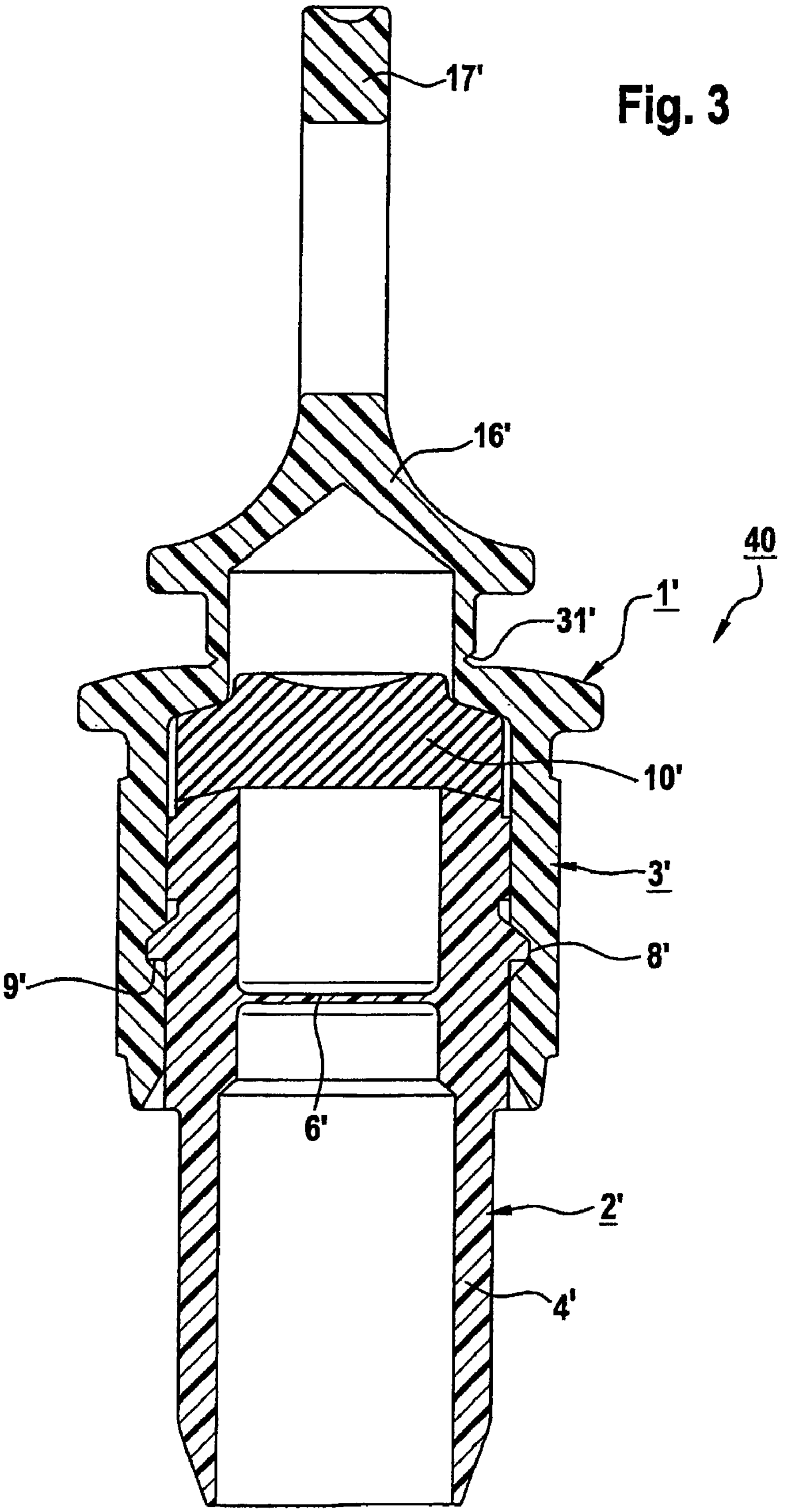

FIG. 3 shows injection part 40 of film bag 21 in a sectional representation. Injection part 40 has a similar structure to extraction part 20. The parts corresponding to one another are therefore provided with the same reference numbers. Injection part 40 has a tubular connection part 1', which consists of a lower and an upper section 2', 3'. The two sections 2', 3' are fixed in a snap-in manner with the interposition of a self-sealing membrane 10', whereby a projecting shoulder 9' of lower section 2' extending from wall 4' engages in a groove 8' of upper section 3'. Flat membrane 6', which can alternatively be curved, is injected into lower section 2'.

Upper section 3' of tubular connection part 1' is again followed, via a circular rupture zone 31', by a cap-shaped break-off part 16', which is continuous with a flat grip part 17'. An arrow 19' pointing downwards is designed as a recess in grip part 17'. Arrows 23' pointing downwards to indicate the flow direction are located on the outer wall of upper section 3' again inside recessed grips 21', formed by projecting webs 22'.

For the extraction of infusion solution, break-off part 16 of extraction part 20 is broken off by turning or breaking the same, so that self-sealing membrane 10 is laid bare. The spike of a known transfer system is pushed into tubular connection part 1 of extraction part 20, as a result of which pre-slit membrane 10 is pierced and membrane 6 curved downwards is penetrated. Trough-shaped recess 13 serves as a guide for the spike. The spike is sealed by circular portion 12 of membrane 10. On account of the special formation of injected membrane 6, the spike is held firmly in tubular connection part 1.

The infusion solution can then be extracted. When the spike is again withdrawn, self-sealing membrane 10 reliably seals extraction part 20 even in the presence of a relatively high internal pressure. Moreover, the mechanical strength of extraction part 20 is increased by the special formation of injected membrane 6.

Injection part 40 serves to inject an active substance into the infusion solution. For this purpose, self-sealing membrane 10' and injected membrane 6' are again pierced with the injection needle of a syringe after removal of break-off part 16'. The injection part is again sealed after withdrawal of the needle.

The invention claimed is:

1. A connector for packages containing medical fluids, comprising a tubular connection part for receiving a spike for the extraction of the fluid, the connection part comprising a lower section and an upper section, said parts being fixed in a snap-in manner, and a package-side lower opening and a connection-side upper opening;

a break-off sealing part that seals the connection-side opening of the connection part; and a self-sealing membrane disposed in the connection part, which can be pierced by the spike for the extraction of the fluid, said self-sealing membrane comprising:

an inner dish-shaped section having a top surface with a central recessed planar portion and an annular wall portion having a first inner face extending up at a first obtuse angle from the planar portion, which can be penetrated by a tubular extraction device;

an inner circular section having a second inner face extending up from the first inner face at a second obtuse angle relative to the planar portion, wherein the second obtuse angle is greater than the first obtuse angle; and an outer circular section for the fixing of the membrane at the extraction point, said outer circular section having a substantially T-shape configuration clamped with elastic deformation of the membrane between the lower section and the upper section during use, wherein the inner circular section is connected to the stem of the T-shape of the outer circular section, wherein the inner circular section and the inner dish-shaped section together form a trough-shaped recess, and wherein the inner circular section of the membrane surrounds the spike in a sealed manner during penetration of the dish-shaped portion.

2. The connector according to claim 1, wherein the material of the dish-shaped portion of the self-sealing membrane is weakened.

3. The connector according to claim 1, further comprising a second membrane capable of being pierced disposed in the connection part beneath the self-sealing membrane to form an intermediate space.

4. The connector according to claim 3, wherein the second membrane capable of being pierced is a one-piece component of the connection part.

5. The connector according to claim 3, wherein the second membrane is curved upwards or downwards.

6. The connector according to claim 1, wherein the sealing part is connected via a circular rupture zone to the connection part.

7. The connector according to claim 1, wherein the sealing part has a grip part comprising an arrow pointing upwards, wherein the arrow is a recess in the grip part.

8. The connector according to claim 1, wherein the lower section of the connection part comprises an arrow pointing upwards, which is a raised structure.

9. Packaging for medical fluids with a connector according to claim 1.

10. The connector according to claim 2, wherein the material of the dish-shaped portion of the self-sealing membrane is pre-slit.

11. The connector according to claim 8, wherein the arrow is designed as a raised structure in a recessed grip.

12. Infusion bag with a connector according to claim 1.

13. Transfusion bag with a connector according to claim 1.

14. A self-sealing membrane for use in extraction points for containers for medical fluids, comprising:

an inner dish-shaped section having a top surface with a central recessed planar portion and an annular wall portion having a first inner face extending up at a first obtuse angle from the planar portion, which can be penetrated by a tubular extraction device;

an inner circular section having a second inner face extending up from the first inner face at a second obtuse angle relative to the planar portion, wherein the second obtuse angle is greater than the first obtuse angle; and an outer circular section for the fixing of the membrane at the extraction point, said outer circular section having a substantially T-shape configuration configured to be clamped with elastic deformation of the membrane between a lower section and an upper section of a connection part, wherein the inner circular section is connected to the stem of the T-shape on of the outer circular section, wherein the inner circular section and the inner dish-shaped section together form a trough-shaped recess, and wherein the inner circular section surrounds the tubular extraction device in a sealed manner during the penetration of the dish-shaped section.

15. The membrane according to claim 14, wherein the material of the inner dish-shaped section is weakened.

16. The membrane according to claim 15, wherein the material of the inner dish-shaped section is slit.

17. The membrane of claim 14, wherein the inner dish-shaped section has a continuous planar bottom surface extending the entire diameter of the inner dish-shaped section.

18. The membrane of claim 14, wherein the first inner face and the second inner face are flat.

19. The connector according to claim 1, wherein the inner dish-shaped section has a planar bottom that extends lower that the bottom of the outer circular section.

* * * * *